United States Patent [19]

Gelb, Jr.

[11] Patent Number: 5,250,298
[45] Date of Patent: * Oct. 5, 1993

[54] LIVE ATTENUATED NEWCASTLE DISEASE VIRUS VACCINES AND PREPARATION THEREOF

[75] Inventor: Jack Gelb, Jr., Landenberg, Pa.

[73] Assignee: University of Delaware, Newark, Del.

[*] Notice: The portion of the term of this patent subsequent to Sep. 19, 2006 has been disclaimed.

[21] Appl. No.: 808,046

[22] Filed: Dec. 12, 1991

Related U.S. Application Data

[63] Continuation of Ser. No. 255,009, Oct. 7, 1988, abandoned.

[51] Int. Cl.$^5$ .......................... A61K 39/12; C12N 7/00
[52] U.S. Cl. ..................................... 424/89; 435/235.1; 435/236; 435/237; 435/948
[58] Field of Search ................ 424/89; 435/235.1, 236, 435/237, 948

[56] References Cited

U.S. PATENT DOCUMENTS

| | | | |
|---|---|---|---|
| Re. 31,831 | 2/1985 | Apontoweil et al. | 424/89 |
| 4,053,583 | 10/1977 | Gits et al. | 424/89 |
| 4,235,876 | 11/1980 | Gits et al. | 424/89 |
| 4,357,320 | 11/1982 | Apontoweil et al. | 424/89 |
| 4,481,188 | 11/1984 | Apontoweil et al. | 424/89 |
| 4,500,638 | 2/1985 | Apontoweil et al. | 435/235 |
| 4,554,158 | 11/1985 | Russell | 424/89 |
| 4,751,079 | 6/1988 | Burger et al. | 424/89 |
| 4,867,975 | 7/1989 | Gelb, Jr. | 424/89 |
| 5,149,530 | 9/1992 | Van Wiltenburg | 424/89 |

FOREIGN PATENT DOCUMENTS 1113860 12/1981 Canada.

OTHER PUBLICATIONS

Gits et al., in Potential as an Aerosol Vaccine of an Improved Newcastle Disease Vaccine Derived from the LaSota Strain-I, In Vitro Studies, *Comp. Immun. Microbiol. Infect. Dis.*, vol. 1, 49-58 (1978).

Zygraich et al. in Potential as an Aerosol Vaccine of an Improved Newcastle Disease Vaccine Derived from the LaSota Strain-II. In Vivo Studies, ibid, 59-66.

Gough et al., Aerosol Vaccination Against Newcastle Disease Using the Ulster Stain, *Avian Pathology* 5:81-95 (1976).

Samburg et al., Spray Vaccination of Chickens with an Experimental Vaccine Against Newcastle Disease, *Avian Pathology*, 6:251-258 (1977).

Kim et al., Administration of a Vaccine Prepared from the Australian V4 Strain of Newcastle Disease Virus by Aerosol and Drinking Water, *Australian Veterinary Journal*, 54, 486-489 (1978).

Villegas et al., Aerosol Vaccination Against Newcastle Disease III. Field Experiments in Broiler Chickens, *Avian Diseases*, vol. 21, No. 1, 16-25 (1979).

Srinivasappa et al., Isolation of a Monoclonal Antibody with Specificity for Commonly Employed Vaccine Strains of Newcastle Disease Virus, *Avian Diseases*, 30:562-567 (1986).

Lana et al. in Characterization of a Battery of Monoclonal Antibodies for Differentiation of Newcastle Disease Virus and Pigeon Paramyxovirus-1 Strains, *Avian Diseases* 32:273-281 (1988).

R. P. Hanson, Chapter 20 of *Isolation and Identification of Avian Pathogens*, edited by Hitchner et al., American Association of Avian Pathologists, Arnold Printing Corporations, Ithaca, N.Y. 14850 (1975), pp. 166-168.

Gelb et al., Improved Respiratory Virus Vaccines for Broilers, *Proceedings of the 23rd National Meeting on Poultry Health and Condemnations*, Oct. 20 and 21, 1988.

*Primary Examiner*—Michael G. Wityshyn
*Assistant Examiner*—Abdel A. Mohamed
*Attorney, Agent, or Firm*—Connolly & Hutz

[57] ABSTRACT

Novel live, cold-adapted temperature-sensitive (CaTs), attenuated Newcastle disease virus vaccines are provided which are effectively immunogenic and contain a mutant of a Hitchner $B_1$ parent strain of Newcastle disease virus.

14 Claims, No Drawings

LIVE ATTENUATED NEWCASTLE DISEASE VIRUS VACCINES AND PREPARATION THEREOF

This application is a continuation of application Ser. No. 07/255,009, filed Oct. 7, 1988, now abandoned.

This invention relates to new live attenuated Newcastle disease virus (NDV) vaccines and a unique process for producing them.

BACKGROUND OF THE INVENTION

The poultry industry is particularly vulnerable to various diseases which plague birds, particularly those caused by respiratory viruses. One of the most enduring of such viruses is Newcastle disease virus.

Generally, the industry controls respiratory disease through vaccination, and virtually all chickens and an increasing number of turkeys produced commercially are vaccinated between one and fourteen days of age to control Newcastle disease.

Newcastle disease virus vaccine is usually combined with vaccines for other respiratory diseases of viral etiology for the convenience of the poultry producer who administers them by drinking water, eyedrop, beak-o-vac ®, or by spray (aerosol). The latter technique is increasing in popularity because it permits mass administration at low labor cost. The problem with this approach is an increase in the severity of Newcastle disease vaccine reactions of chickens, particularly broilers, resulting in a higher incidence of airsac disease, stunted growth, and mortality. In commercial chickens, a number of factors may exacerbate Newcastle disease vaccine reactions including infectious bursal disease virus, Marek's disease virus, and perhaps other agents that may decrease immune function and overall resistance, thus causing the attenuated vaccines to be more pathogenic for immune-compromised chickens. Hatchery-related bacterial and fungal infections are also an important consideration since they predispose baby chicks to more severe vaccine reactions.

In 1977, U.S. Pat. No. 4,053,583 described a mutagenic treatment of a parent virus strain by ultraviolet irradiation or treatment with buffered nitrous acid solution. The mutagenic treatment is pathogenic to animals (including humans) and virus alike, and inactivates most of the parent virus population. The surviving virus is isolated and cold adapted at 26° C., followed by cloning at the cold adaptation temperature. Despite the claims of effectiveness for the product strain, the inventors issued U.S. Pat. No. 4,235,876 in 1980 in which they acknowledge the low infectivity of the strain produced and teach that the infectivity of at least one strain improves when the virus is treated with trypsin or passaged twice on chicken embryo fibroblasts at a non-permissive temperature of 41° C. The passage of time has shown that neither the mutagenic treatment nor the modified mutagenic treatment provides an adequate answer to the problem of Newcastle disease virus vaccination.

A recent trend in the United States is to discontinue the use of inactivated adjuvant-based Newcastle disease virus vaccines in broiler breeders. Breeder hens vaccinated with inactivated vaccines confer high levels of maternal antibody to their chicks. However, Newcastle disease virus maternal antibody interferes to varying degrees with Newcastle disease virus vaccinations during the first week of life and some chicks with low Newcastle disease virus maternal antibody titers experience more severe vaccine reactions. Young broilers will suffer an increase in vaccine reactions and mortality associated with Newcastle disease virus vaccines as a result of diminished use of inactivated Newcastle disease virus vaccine.

A common response of the poultry producer to increased early vaccine reaction problems has been to cut or dilute respiratory virus vaccines. This is a risky practice, particularly when mass vaccination methods such as coarse spray or drinking water applications are used since chickens thus vaccinated are less likely to receive an adequate immunizing dose of the vaccine virus and contract the vaccine virus from a vaccinated flockmate. Bird-to-bird transmission of respiratory vaccine viruses increases virus pathogenicity and contributes to extended "rolling" reactions since chicks become infected at different times. The normal decay of maternal antibody to Newcastle disease virus and infectious bronchitis virus (IBV) also plays a role in "rolling" reactions since chicks missed during vaccination become more susceptible to vaccine reactions the later they become infected.

Consequently, an adequate Newcastle disease virus vaccine administrable to animals, including poultry, by spray (aerosol) is not yet available.

SUMMARY OF THE INVENTION

Novel live, cold-adapted temperature-sensitive (CaTs), attenuated Newcastle disease virus vaccines have now been found which are effectively immunogenic yet non-pathogenic to animals, particularly poultry, even when administered by spray (aerosol). The vaccines contain a mutant of a Hitchner $B_1$ parent strain of Newcastle disease virus (described below) which is identified by microorganism accession number ATCC VR 2213. Deposit was made on Jun. 29, 1988 with the American Type Culture Collection, Rockville, Md.

Newcastle disease virus vaccines of the invention are prepared by cloning the Hitchner $B_1$ parent virus strain obtained from R. P. Hanson at the University of Wisconsin at Madison, preferably by plaque purification, and serially passaging the cloned virus at a temperature in the range of from about 28° to about 30° C., preferably 29° C., for about ten to about 100 passages, preferably about 20 to 50 passages, most preferably 36 passages, through a suitable culture medium. The temperature range comprises a lower than normal growth temperature for the vaccine. Normal vaccine growth temperature is about 37° C.

The live CaTs Newcastle disease virus vaccine of the invention attenuated from the parent Hitchner $B_1$ strain is then harvested. The harvested or isolated virus vaccine can then be freeze-dried for storage or combined in a suitable, preferably pharmaceutically acceptable, carrier, extender, or diluent, referred to herein collectively as "extender", for administration to animals, particularly poultry, by any suitable means including eyedrop, drinking water, beak-o-vac ® or spray (aerosol). Administration by spray or aerosol is preferred. The process of the invention produces live attenuated Newcastle disease virus vaccines without mutagenic treatment and provides a milder alternative to commercial vaccines for immunizing animals, particularly poultry, against Newcastle disease.

Dosages of from about log 4 to log 7 embryo infectious dose$_{50}$ (EID$_{50}$) per animal are recommended, especially for poultry, and from log 4.5 to 6.5 are preferred, with 4.5 most preferred. Higher dosages may be needed if the vaccine is freeze-dried and stored for an extended period of time.

An effective amount of the CaTs vaccines of the invention to immunize an animal, particularly poultry, against Newcastle disease virus provides a high level of immunity with a low level of disease, even when used in a mixture with other vaccines whether administered by eyedrop or spray or any other appropriate method. This is particularly surprising since the process does not employ chemical or physical (e.g. ultraviolet irradiation) mutagenic treatment of the virus in the development of the cold-adapted strain, and such results have not been obtainable heretofore.

DETAILED DESCRIPTION OF THE INVENTION

Virtually all Hitchner $B_1$ virus strains are derived from the original strain isolated by Hitchner. The source of the parent Hitchner $B_1$ strain used in the fabrication of the CaTs virus vaccine of the invention is R. P. Hanson, Newcastle Disease Virus Repository, Department of Veterinary Science, University of Wisconsin, at Madison, Wis.

The Hitchner $B_1$ strain is cloned to obtain a relatively pure strain before it is cold-adapted. The cloning process involves the isolation of plaques formed on primary chicken kidney cell cultures incubated at about 37° C. Cloning may also be performed by the limit dilution method in a suitable host system (e.g. cell culture or embryonated eggs).

At this point, the cloned virus has no temperature-sensitive properties and is strongly pathogenic. It is inoculated via the chorioallantoic sac route into nine- to eleven-day-old specific-pathogen-free (SPF) chicken embryos which have been incubated at about 29° C. for about six hours prior to inoculation. The amniotic-allantoic fluids are then harvested at from about 72-120 hours after inoculation and successively passaged through a suitable culture medium, such as embryonated SPF chicken eggs, at lower than normal temperature, generally from about 28° to about 30° C., preferably 29° C. The harvested virus-containing amniotic-allantoic fluids may be diluted from $10^{-1}$ to $10^{-6}$. The lower dilutions (e.g. $10^{-1}$) can give better virus yields in lower passages (up to about passage 20) as the virus becomes cold-adapted. Higher dilutions of the fluids (e.g. up to about $10^{-6}$) are preferably used for from about passage 20 to 36. U.S. Pat. No. 4,554,158 describes serial passaging in detail and is incorporated by reference herein for that disclosure. After twenty passages, the virus begins to develop temperature-sensitive characteristics. Although up to about 100 passages can be carried out at the lower than normal temperatures of this invention, it is ordinarily preferred to limit the number of passages to something less than 100 to obtain optimum immunogenic response. Accordingly, from about 20 to about 50 passages are preferred and 36 is most preferred.

The live, attenuated Newcastle disease virus vaccine thus produced is cold-adapted and temperature-sensitive. This is important since upper respiratory tract tissues such as the trachea, gland of Harder, and others important in the induction of local tissue immunity and vital to the development of protective immunity, have a temperature lower than 41° C., the temperature of the deep internal organs, due to evaporative cooling from respiratory mucous membranes. The cold-adapted, temperature-sensitive respiratory virus vaccines of the invention can grow in the cells of the upper respiratory tissues and induce local tissue immunity because they grow at temperatures lower than 41° C. Further, the temperature-sensitive virus vaccines of the invention replicate well at a normal growth temperature such as 37° C. but grow poorly at high temperatures, such as a temperature close to the internal temperature of a chicken (about 41° C.). As a result, the temperature-sensitive strains of the invention are able to multiply at cooler sites of the body while replication is inhibited in the deep warm organs of the host. Viruses that are not cold-adapted and not temperature-sensitive (nonCaTs) grow equally well at 41° C. as at normal growth temperature of about 37° C.

The cold-adapted, temperature-sensitive, live, attenuated Newcastle disease virus vaccine of the invention can be isolated or harvested and freeze-dried for storage or combined with a suitable extender for administration by any suitable means, including eyedrop, drinking water, beak-o-vac ®, and spray/aerosol techniques. The vaccine of the invention is particularly adapted to be administered by spray or aerosol since it is particularly adapted to be administered by spray or aerosol since it does not induce the degree of respiratory stress normally associated with other vaccines thus administered.

Conventional equipment that aerosolizes a liquid can be used to administer the vaccines of the invention. Hatchery spray cabinets for day-old broilers marketed by Sterwin and characterized as "cross-fire" spray cabinets can deliver droplets of predetermined size. Droplet sizes of about 400 microns in diameter delivered at an air pressure of about 30 pounds per square inch at an angle of about 65° provides safe, effective dosing and are preferred. Spraying in the hatchery cabinets permits the vaccination of about 100 chicks simultaneously without the labor required when individual animals are vaccinated by other methods.

The unique CaTs p36 Newcastle disease virus $B_1$ strain of the invention is deposited at the American Type Culture Collection and has received ATCC designation VR 2213.

The cold-adapted and temperature-sensitive characteristics of the virus of the invention are distinguishing properties and have practical significance as markers for vaccine virus production and quality control. Another unique characteristic by which the CaTs vaccine of the invention can be differentiated from other $B_1$ strains, and particularly from non-CaTs NDV vaccines, is that they react differently with a well-characterized monoclonal antibody (AVS-I) described by Srinivasappa et al in Isolation of a Monoclonal Antibody with Specificity for Commonly Employed Vaccine Strains of Newcastle Disease Virus, *Avian Diseases*, 30: 562–567 (1986). The fact that monoclonal antibody AVS-I has a high binding affinity for all $B_1$ and LaSota strains of NDV, including vaccines, has been confirmed by Lana et al in Characterization of a Battery of Monoclonal Antibodies for Differentiation of Newcastle Disease Virus and Pigeon Paramyxovirus-1 Strains, *Avian Diseases*, 32: 273–281 (1988). Lana et al disclose that the monoclonal antibody AVS-I generated by Srinivasappa et al reacts to high titers in hemagglutination-inhibition (HI) tests exclusively with NDV lentogenic strains, thereby demonstrating immunodiagnostic capability. However, although the CaTs vaccine of the invention is lentogenic, it is not recognized by the AVS-I monoclonal antibody. By contrast, the non-CaTs $B_1$ virus vaccine is clearly recognized by the AVS-I monoclonal antibody in the HI test as shown in Example 9 below. This unique characteristic of the vaccines of the invention provides unexpected advantages over other vaccines known in the art.

The vaccine of the invention displays cold-adapted, temperature-sensitive, and immunogenic properties without the pathogenicity characteristic of non-temperature-sensitive vaccines as illustrated by the pathogenicity and immunogenicity studies of Examples 5-8. Thus, the CaTs vaccine of the invention is safer than current conventional vaccines and provides a major benefit to the poultry industry. The general health of birds has been shown to improve with sharply reduced stress from disease resulting in less stunted growth, fewer complications from bacteria, and lower overall mortality.

The cold-adapted, temperature-sensitive, live, attenuated Newcastle disease virus vaccine of the invention can be used at any suitable dosage but dosages of from about log 4 to log 7 embryo infectious dose$_{50}$ per animal are recommended, especially for poultry, and from log 4.5 to 6.5 is preferred, with 4.5 most preferred. Higher dosages (e.g. 6.0) are generally preferred if the vaccine is freeze-dried and stored for an extended period of time.

The vaccines of the invention can be combined with other vaccines using any suitable technique provided that there is no reaction between the vaccines or other interference with desired efficacy. When the vaccines are to be sprayed, it is conventional to combine live vaccines only. When vaccination is to be carried out by injection, killed vaccines are generally used as boosters after live vaccines have been administered. Some suitable vaccines that can be combined with the vaccines of the invention include avian infectious respiratory disease virus vaccines, preferably infectious bronchitis virus vaccines such as those disclosed in copending application Ser. No. 148,987 incorporated herein by reference. A preferred mutant of the Arkansas-type DPI strain of avian infectious bronchitis virus is identified by the microorganism accession number ATCC VR 2200. Examples of other vaccines which can also be combined with the vaccines of the invention include those disclosed in U.S. Pat. Nos. 4,500,638; 4,481,188; 4,357,320; 4,053,583; 4,235,876; and U.S. Pat. No. Re. 31,839, hereby incorporated by reference. Vaccines to treat infectious laryngotracheitis virus, infectious bursal disease virus, avian adenoviruses and other respiratory viruses can also be administered in a mixture with the vaccines of the invention by any suitable method.

The invention is further illustrated but is not intended to be limited by the following examples in which the CaTs vaccine of the invention is prepared from the parent Hitchner $B_1$ strain by cold adaptation at 29° C. for 36 passages. The non-CaTs vaccine is prepared by 36 passages at 37° C.

EXAMPLE 1

This example illustrates the temperature sensitivity of the cold-adapted temperature-sensitive (CaTs) Newcastle Disease Virus (NDV) vaccines of the invention. Ten-fold serial dilutions of CaTs NDV ($10^{-1}$–$10^{-10}$) in sterile tryptose phosphate broth containing 100 IU penicillin and 100 μg streptomycin per ml are prepared. Ten- to eleven-day-old SPF (specific-pathogen-free) chickens embryos that have been incubated for 18-24 hours at 37° C. or 41° C. are inoculated via the chorioallantoic sac route with 0.2 ml of each virus dilution. The embryos are incubated for seven days and then placed at 4° C. The embryos are examined for lesions (stunting and hemorrhage of the skin). The allantoic fluids are tested for evidence of NDV by a hemagglutination test. Embryos that display stunting and/or hemorrhage or a positive hemagglutination reaction of the allantoic fluids are considered NDV positive. The infectious virus titer of the CaTs vaccine of the invention and a non-CaTs strain derived from the same parent Hitchner $B_1$ strain is shown in Table 1.

The results indicate that the CaTs vaccine is temperature-sensitive since it grows very poorly at the elevated temperature of 41° C.

TABLE 1

| Virus | Titration Temperature | | Change in Virus Titer |
|---|---|---|---|
| | 37° C. | 41° C. | |
| CaTs $B_1$ | 9.2$^A$ | 1.9 | 7.3 |
| Non-CaTs $B_1$ | 9.9 | 9.3 | 0.6 |

A = Virus expressed as log embryo infectious dose$_{50}$ per ml.

EXAMPLE 2

This example illustrates the cold-adapted property of the CaTs NDV vaccines of the invention. Thirty ten- to eleven-day-old SPF chicken embryos are inoculated via the chorioallantoic sac with each of 0.2 ml containing $10^3$ EID$_{50}$ of CaTs and non-CaTs NDV vaccine at 29° C. Five eggs are removed from the incubators at 12, 24, 48, 72, 96 and 120 hours after inoculation and placed at 4° C. overnight. The amniotic-allantoic fluids from each of the five eggs are harvested, pooled, and stored at −70° C. Virus titration of the harvested amniotic-allantoic fluids are performed by preparing serial ten-fold dilutions of the egg fluids in sterile tryptose phosphate broth containing antibiotics. Ten- to eleven-day-old embryos are inoculated via the chorioallantoic sac and are incubated at 37° C. for seven days. Results are shown in Table 2.

TABLE 2

| Virus | Incubation Temp (°C.) | Hours Postinoculation | | | | | |
|---|---|---|---|---|---|---|---|
| | | 12 | 24 | 48 | 72 | 96 | 120 |
| CaTs $B_1$ | 29 | 3.6$^A$ | 6.2 | 10.2 | 11.0 | 10.4 | 10.2 |
| NonCaTs $B_1$ | 29 | 2.5 | 3.4 | 7.2 | 9.4 | 10.0 | 10.4 |

A = Virus titer (log embryo infectious dose$_{50}$ per ml) determined by titration in embryonated chicken eggs incubated at 37° C.

The results indicate that the CaTs vaccine is cold-adapted since it grows more rapidly at 29° than the non CaTs virus.

EXAMPLE 3

This example illustrates how rapidly the virus elutes from avian erythrocytes. The procedure is carried out at 4° C. A standard hemagglutination test is prepared and hemagglutination titer is determined after the chicken erythrocytes settle. Incubation is continued for 24 hours when the titer is read again. The erythrocytes are then resuspended and the titer is read after 2 hours. Some strains render the erythrocytes unagglutinable in all dilutions at 24 hours, before and after resuspension (rapid eluter). The virus of other strains continued to be attached to the cells and the agglutination persists for 24 hours, both before and after resuspension (slow eluter).

In a few instances, agglutination fails to persist after resuspension (intermediate eluter).

TABLE 3

| Virus | Elution Rate |
|---|---|
| CaTs | Rapid, less than 2 hr |
| NonCaTs | Rapid, less than 2 hr |
| Hitchner B₁ | Rapid, less than 2 hr |
| LaSota | Slow, greater than 24 hr |

As the results suggest, the elution rate is a method for differentiating the Hitchner B₁ strain from other strains. The CaTs and non-CaTs viruses derived from the Hitchner B₁ strain also have a rapid elution rate.

EXAMPLE 4

The mean death time of the minimal lethal dose (MDT/MLD) of chicken embryos is shown in this example. As already described, tenfold serial dilutions ($10^{-1}$–$10^{-10}$) are prepared and the five highest dilutions of the CaTs and several other viruses representing different NDV pathotypes are each inoculated into ten, nine-day-old embryos, five receiving the inoculum in the morning and five in the afternoon. This inoculation schedule adjusts, in part, for the usual observation schedule of morning and evening candling which gives hourly intervals of 8, 16, 8, 16, 8, etc. However, an approximation of MDT/MLD can be obtained with a single inoculation even when a skewed candling schedule is followed. Results are shown in Table 4.

TABLE 4

| NDV Strain | MDT/MLD (hours) |
|---|---|
| CaTs B₁ | 140 |
| Non-CaTs B₁ | 107 |
| Hitchner B₁ (lentogenic) | 121 |
| Roakin (mesogenic) | 72 |
| Texas GB (velogenic) | 60 |

The CaTs B₁, non-CaTs B₁, and Hitchner B₁ viruses had MDT/MLD of greater than 100 hours indicating that they are lentogenic strains of NDV. Lentogenic strains are of low pathogenicity for chickens, mesogenic strains are of intermediate pathogenicity, and velogenic strains are of high pathogenicity for chickens.

EXAMPLE 5

The pathogenicity of the CaTs NDV vaccine of the invention is evaluated in one-day-old commercial broiler chickens in this example. One-hundred one-day-old commercial broiler chickens are obtained from a hatchery. The chickens are wingbanded and inoculated with $10^6$ EID₅₀ per chicken via the intratracheal route. The chickens inoculated with the viruses identified in Table 5 are placed in separate colony houses on clean litter and provided a commercial diet. The chickens are observed daily for 14 days and evaluated for signs of clinical respiratory disease (sneezing, coughing, rales, labored breathing) and mortality. Table 5 gives the clinical disease responses of the chickens on a daily basis. Pathogenicity of the CaTs NDV vaccine of the invention, non-CaTs and Hitchner B₁ strains is shown in Table 6. The pathogenicity of CaTs B₁ was clearly less than the non-CaTs B₁ and the Hitchner B₁ as indicated by a lower pathogenicity index and incidence of disease (air sac lesions) associated with vaccination.

TABLE 5

| Virus Treatment | Day Postinoculation | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| CaTs B₁ [A] | 0/20 | 0/20 | 0/20 | 0/20 | 1/20 | 1/20 | 3/20 | 4/20 | 3/20 | 4/20 | 1/20 | 2/20 | 2/20 | 0/20 |
| CaTs B₁ [B] | 0 | 0 | 0 | 0 | 5 | 5 | 15 | 20 | 15 | 20 | 5 | 10 | 10 | 0 |
| NonCaTs B₁ [A] | 0/20 | 0/20 | 10/20 | 17/20 | 17/20 | 18/20 | 18/20 | 18/20 | 18/20 | 8/20 | 3/20 | 3/20 | 3/20 | 1/20 |
| NonCaTs B₁ [B] | 0 | 0 | 50 | 85 | 85 | 90 | 90 | 90 | 90 | 40 | 15 | 15 | 15 | 5 |
| Hitchner B₁ [A] | 0/20 | 3/20 | 8/20 | 15/20 | 17/20 | 18/20 | 19/20 | 19/20 | 19/20 | 7/20 | 5/20 | 3/20 | 3/20 | 3/20 |
| Hitchner B₁ [B] | 0 | 15 | 40 | 75 | 85 | 90 | 95 | 95 | 95 | 35 | 25 | 15 | 15 | 15 |
| None [A] | 0/20 | 0/20 | 0/20 | 0/20 | 0/20 | 0/20 | 0/20 | 0/20 | 0/20 | 0/20 | 0/20 | 0/20 | 0/20 | 0/20 |
| None [B] | 0 | 0 | 0 | 0 | 0 | 0 | 0 | 0 | 0 | 0 | 0 | 0 | 0 | 0 |

[A] Number of chickens with respiratory disease signs (coughing, sneezing, tracheal rales, congestion or labored breathing) or death/total.
[B] Percent of chickens exhibiting respiratory disease signs including death.

TABLE 6

| Virus Treatment | Mortality (%) | Airsac Lesions[A] % | Pathogenicity Index[B] |
|---|---|---|---|
| CaTs B₁ | 0/20 (0%) | 1/20 (5%) | .075 |
| Non-CaTs B₁ | 1/20 (5%) | 6/20 (30%) | .296 |
| Hitchner B₁ | 2/20 (10%) | 13/20 (65%) | .478 |
| None | 0/20 (0%) | 0/20 (0%) | 0 |

[A] = Number of chickens with airsacculitis, perihepatitis or pericarditis/total.
[B] = Pathogenicity index calculated for 14 day postinoculation observation period. Pathogenicity index = sum of scores/number of observations.
Scores:
Morbidity = 1,
mortality = 2.

EXAMPLE 6

The comparative pathogenicity of the CaTs NDV vaccine of the invention and seven commercial B₁ vaccines is investigated in this Example. Commercial NDV B₁ strain vaccines are obtained from seven manufacturers. The vaccines are titrated in ten- to eleven-day-old SPF embryonated eggs inoculated via the chorioallantoic sac route. The lyophilized vaccines are rehydrated in 30 ml tryptose phosphate broth containing antibiotics. Dilutions of $10^{-1}$ to $10^{-10}$ are prepared and 0.2 ml (3 embryos per dilution) are inoculated via the chorioallantoic sac. The titration eggs are incubated at 37° C. for 7 days. EID₅₀ virus titers are calculated for the vaccines.

Eight groups of twenty, seven-day-old SPF chickens are vaccinated intratracheally with $10^6$ EID₅₀ of the different B₁ NDV vaccines. Seven groups receive commercially available B₁ vaccines, each from a different manufacturer. Another virus-vaccinated group is given CaTs NDV vaccine similarly. An unvaccinated negative control group is maintained for comparative purposes. All chickens are scored daily for respiratory disease signs as in Example 5. At 14 days post-vaccination, the chickens are sacrificed and examined for airsac lesions.

Pathogenicity indexes for the seven commercial B₁ NDV vaccines ranged from two to five times higher than that of the CaTs vaccine of the invention. Further, the incidence of air sac lesions in chickens that received the commercial B₁ vaccines is five to 14 times higher than for chickens that received the CaTs NDV vaccine of the invention. Such results show that the vaccines of the invention are less pathogenic for chickens than all the commercial vaccines tested.

EXAMPLE 7

The efficacy of the CaTs NDV vaccine of the invention for commercial broiler chickens is shown in this example. Sixty-six one-day-old commercial broiler chickens are obtained from a hatchery and held in isolation for one week. The seven-day-old birds are wingbanded and assigned to three groups and vaccinated with the vaccine of the invention by eyedrop as shown in Table 7. At 21 days post-vaccination, all the chickens are challenged with $10^5$ ELD$_{50}$ per bird of the Texas GB strain of NDV by eyedrop. The birds are observed daily for ten days for central nervous system signs and mortality.

TABLE 7

| Vaccine | Dose per Chicken (log) | Postchallenge Disease/Mortality | |
|---|---|---|---|
| CaTs B$_1$ | 5.5 | 1/22[A] | (95%)[B] |
| CaTs B$_1$ | 6.5 | 1/21 | (95%) |
| None | — | 23/23 | (0%) |

A - Number of chickens with central nervous system signs or dead/total.
B - Percent protection.

EXAMPLE 8

The efficacy of the vaccine of the invention for SPF white leghorn chickens is investigated in this example. Seventy-five two-week-old SPF white leghorn chickens are assigned to five groups of fifteen chickens and wingbanded. The chickens are vaccinated by eyedrop with $10^{3.5}$, $10^{4.5}$, $10^{5.5}$ and $10^{6.5}$ embryo infectious dose$_{50}$ of CaTs NDV of the invention per bird. One group remains unvaccinated. The birds are housed in separate isolators according to treatment group.

Three weeks after vaccination, all chickens are challenged by eyedrop with $10^4$ ELD$_{50}$ of the neurotropic-velogenic Texas GB strain of NDV. The chickens are observed daily for ten days for central nervous system signs and mortality.

The results show that the CaTs vaccine produces a high degree of protection when given at a doseage equal to or greater than $10^{4.5}$ embryo infectious dose$_{50}$ per chicken.

TABLE 8

| Vaccine Dose[A] | Postchallenge Disease/Mortality | |
|---|---|---|
| 6.5 | 0/15[B] | (100%)[C] |
| 5.5 | 0/15 | (100%) |
| 4.5 | 1/15 | (93%) |
| 3.5 | 10/15 | (33%) |
| None | 15/15 | (0%) |

A - Expressed as log embryo infectious dose$_{50}$ per chicken.
B - Number of chickens with central nervous system signs or dead/total.
C - Percent protection.

EXAMPLE 9

The reactivity of several well-characterized NDV monoclonal antibodies and the CaTs NDV vaccine of the invention as well as its non-CaTs counterpart are evaluated using the hemagglutination-inhibition (HI) test.

Monoclonal antibody AVS-I has been shown previously by Srinivasappa et al in *Avian Diseases* 30: 562–567, 1986, herein incorporated by reference to react specifically and extensively in the HI test with commercial B$_1$ and LaSota strain vaccines. Lana et al in *Avian Diseases* 32: 273–281, 1988 herein incorporated by reference confirmed that finding by Srinivasappa et al and reported on the preparation and reactivity of several other monclonal ant:[bodies, 79, 15C4, and 10D11, in addition to AVS-I. Antibody 79 reacts extensively with all NDV strains of chicken and pigeon origin. Antibody 15C4 reacts extensively with all NDV strains of chicken origin only. Antibody 10D11 reacts extensively with neurotropic velogenic strains and to a lesser but readily detectable level with mesogenic strains.

TABLE 9

| Antibody | | Virus | |
|---|---|---|---|
| Identification | Type | CaTs | non-CaTs |
| AVS-I | monoclonal | <10[A] | 320 |
| 10D11 | monoclonal | <10 | <10 |
| 79 | monoclonal | 5120 | 5120 |
| 15C4 | monoclonal | 320 | 320 |
| Positive | polyclonal | 2560 | 2560 |
| Negative | serum | <10 | <10 |

A - HI antibody titers expressed as the reciprocal of a polyclonal serum or monoclonal ascitic fluid dilution.

Surprisingly, the above results of HI tests using CaTs vaccine of the invention and non-CaTs virus indicate that the AVS-I monoclonal antibody does not react and therefore does not recognize CaTs B$_1$ vaccine. This is an unexpected finding since the CaTs B$_1$ strain is lentogenic (Example 4) and a rapid eluting strain (Example 3). Thus, the inability of the CaTs B$_1$ vaccine to react with AVS-I is an important marker that differentiates CaTs B$_1$ vaccine from other B$_1$ and LaSota vaccines.

As expected, however, HI test results using other monclonal antibodies 79, 15C4, and 10D11 show the CaTs vaccine and non-CaTs virus to be NDV strains but not related to neorotropic velogenic strains or mesogenic strains of chicken origin. Furthermore, the CaTs NDV vaccine is not of pigeon origin.

EXAMPLE 10

SPF white leghorn chickens are vaccinated in a "cross-fire" spray cabinet manufactured by Sterwin Laboratories using the CaTs vaccine of the invention. Two flat spray nozzles, each emitting 3.5 ml of vaccine per 100 chickens, provides about $10^{6.5}$ EID$_{50}$ per chick in sterile distilled water in spray droplets of about 400 microns in diameter at an air pressure of about 30 pounds per square inch and at an angle of about 65°.

One-hundred, one-day-old chickens are placed in a chick box. The box is pushed into the spray cabinet, thereby engaging the spray system activating lever to turn on a spray that vaccinates the chickens with the CaTs B$_1$ vaccine of the invention. The vaccinated chicks and the chick box are removed from the spray cabinet. The CaTs-vaccinated chicks and a group of unvaccinated control chicks are placed in different colony houses.

Four weeks after vaccination, all of the chicks are challenged by intramuscular inoculation with 0.2 ml of the Texas GB strain of NDV at a concentration of $10^4$ ELD$_{50}$ in sterile broth. The chickens are observed daily for ten days for central nervous system signs and mortality. Chickens vaccinated with the CaTs B$_1$ vaccine are protected and do not show any disease signs or mortality. All of the unvaccinated control chickens become paralyzed or die. These results demonstrate that the administration of the CaTs vaccine of the invention by spray is highly efficacious.

Although the invention has been described in considerable detail in the foregoing, it is to be understood that such detail is for purposes of illustration only and that variations can be made by one skilled in the art without departing from the spirit and scope of the invention, except as set forth in the claims.

What is claimed is:

1. A mutant of the Hitchner $B_1$ strain or Newcastle disease virus identified by microorganism accession number ATCC VR 2213, wherein the mutant virus is less able to replicate at 41° C. than at 37° C.

2. A live, cold-adapted, temperature sensitive Newcastle disease virus vaccine comprising the mutant of claim 1 in a pharmaceutically acceptable extender.

3. A live, cold-adapted, temperature sensitive Newcastle disease virus vaccine for poultry, comprising from log 4 to log 7 embryo infectious dose$_{50}$ per bird of the mutant of claim 1 in a pharmaceutically acceptable extender.

4. A live, cold-adapted, temperature sensitive Newcastle disease virus vaccine for poultry comprising from log 4.5 to log 6.5 embryo infectious dose$_{50}$ per bird of the mutant of claim 1 in a pharmaceutically acceptable extender.

5. A live, cold-adapted, temperature sensitive Newcastle disease virus vaccine for poultry comprising log 4.5 embryo infectious dose$_{50}$ per bird of the mutant of claim 1 in a pharmaceutically acceptable extender.

6. A method for immunizing a poultry against Newcastle disease virus which comprises administering to the poultry the vaccine of claim 3.

7. The method of claim 6 wherein the vaccine is administered by spray.

8. A method for making a live, cold-adapted, temperature-sensitive Newcastle disease virus vaccine which comprises cloning a Hitchner $B_1$ Newcastle disease virus strain, serially passaging the cloned virus from 20 to 100 times through a culture medium at a lower than normal temperature of from 28 degrees C to 30 degrees C, and harvesting the resulting cold-adapted, temperature sensitive mutant.

9. The method of claim 8 wherein the harvested mutant is freeze-dried.

10. The method of claim 8 wherein the harvested mutant is combined with an extender.

11. The method of claim 10 wherein the mutant is combined with the extender at a dosage of from log 4 to log 7 embryo infectious dose$_{50}$ per bird.

12. The method of claim 8 wherein the cloned virus is passaged for from 20 to 50 passes at a lower than normal temperature of about 29° C.

13. The method of claim 12 wherein the cloned virus is passaged for 36 passes.

14. A live, cold-adapted temperature-sensitive Newcastle disease virus vaccine produced by the method of claim 8, wherein the mutant virus is less able to replicate at 41° C. than at 37° C.

* * * * *